United States Patent
Sullivan et al.

(10) Patent No.: US 9,767,667 B2
(45) Date of Patent: *Sep. 19, 2017

(54) SYSTEMS AND METHODS FOR MONITORING PHYSIOLOGY WITH UNABLE-TO-MEASURE ALERTS

(71) Applicant: HOANA MEDICAL, INC., Honolulu, HI (US)

(72) Inventors: Patrick K. Sullivan, Kailua, HI (US); Matthew S. Glei, Honolulu, HI (US); Paul M. Embree, Tustin, CA (US); Shashidhar B. Hebsur, Palo Alto, CA (US); Nicholas C. Epperson, Honolulu, HI (US)

(73) Assignee: HOANA MEDICAL, INC., Honolulu, HI (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/045,153

(22) Filed: Feb. 16, 2016

(65) Prior Publication Data
US 2016/0171867 A1 Jun. 16, 2016

Related U.S. Application Data

(60) Division of application No. 14/252,748, filed on Apr. 14, 2014, now Pat. No. 9,275,533, which is a
(Continued)

(51) Int. Cl.
*G08B 23/00* (2006.01)
*G08B 21/04* (2006.01)
(Continued)

(52) U.S. Cl.
CPC ........ *G08B 21/0461* (2013.01); *A61B 5/0002* (2013.01); *A61B 5/002* (2013.01);
(Continued)

(58) Field of Classification Search
CPC .. A61B 5/7282; A61B 5/002; G08B 21/0461; G08B 21/22
(Continued)

(56) References Cited

U.S. PATENT DOCUMENTS

| 4,320,766 A | 3/1982 | Alihanka et al. |
| 4,509,527 A | 4/1985 | Fraden |

(Continued)

*Primary Examiner* — Tai T Nguyen
(74) *Attorney, Agent, or Firm* — Fulwider Patton LLP

(57) ABSTRACT

A system that observes and analyzes, and, only in the event of a significant negative condition, notifies and reports the event. In a hospital environment, the device includes a bedside unit connected to a pad or coverlet with a sensor array (placed under the patient) and also to an existing hospital nurse call system via an interface. The bedside unit is a wall-mounted unit with a display that becomes active when an alarm condition is enabled. Vigilance alarms are suspended if a patient is detected out of bed. An unable-to-measure alert is provided if the system is unable to reliably monitor. An alert message is generated and maintained on the display screen to inform a responding caregiver of the time and reason for any alarm. The system also may be adapted for use as a monitoring system for operators of motor vehicles, aircraft or other devices.

32 Claims, 9 Drawing Sheets

Related U.S. Application Data continuation of application No. 12/617,652, filed on Nov. 12, 2009, now Pat. No. 8,698,635, and a division of application No. 11/624,207, filed on Jan. 17, 2007, now Pat. No. 7,629,890, and a continuation-in-part of application No. 11/004,589, filed on Dec. 3, 2004, now Pat. No. 7,304,580.

(60) Provisional application No. 60/526,612, filed on Dec. 4, 2003.

(51) Int. Cl.
| | | |
|---|---|---|
| *A61B 5/00* | (2006.01) | |
| *G08B 21/02* | (2006.01) | |
| *A61B 5/11* | (2006.01) | |
| *A61G 12/00* | (2006.01) | |
| *G08B 21/22* | (2006.01) | |
| *A61B 5/01* | (2006.01) | |
| *A61B 5/0205* | (2006.01) | |
| *A61B 5/0245* | (2006.01) | |
| *A61B 5/08* | (2006.01) | |
| *A61B 5/18* | (2006.01) | |
| *B60W 40/08* | (2012.01) | |

(52) U.S. Cl.
CPC .......... *A61B 5/1115* (2013.01); *A61B 5/6892* (2013.01); *A61B 5/6893* (2013.01); *A61B 5/7207* (2013.01); *A61B 5/7282* (2013.01); *A61B 5/743* (2013.01); *A61B 5/746* (2013.01); *A61G 12/00* (2013.01); *G08B 21/02* (2013.01); *G08B 21/22* (2013.01); *A61B 5/01* (2013.01); *A61B 5/0205* (2013.01); *A61B 5/02455* (2013.01); *A61B 5/0816* (2013.01); *A61B 5/18* (2013.01); *A61B 2562/0247* (2013.01); *A61B 2562/046* (2013.01); *B60W 2040/0872* (2013.01)

(58) Field of Classification Search
USPC .......... 340/576, 575, 511; 600/483, 508, 509
See application file for complete search history.

(56) References Cited

U.S. PATENT DOCUMENTS

| | | | |
|---|---|---|---|
| 4,664,124 A | | 5/1987 | Ingle et al. |
| 4,827,763 A | | 5/1989 | Bourland et al. |
| 4,926,866 A | | 5/1990 | Lee |
| 5,002,060 A | | 3/1991 | Nedivi |
| 5,078,134 A | * | 1/1992 | Heilman .............. A61B 5/6831 600/508 |
| 5,137,033 A | | 8/1992 | Norton |
| 5,144,284 A | | 9/1992 | Hammett |
| 5,353,793 A | | 10/1994 | Bornn |
| 5,416,469 A | | 5/1995 | Colling |
| 5,448,996 A | | 9/1995 | Bellin et al. |
| 5,585,785 A | | 12/1996 | Gwin et al. |
| 5,590,650 A | | 1/1997 | Genova |
| 5,724,025 A | | 3/1998 | Tavori |
| 5,808,552 A | | 9/1998 | Wiley et al. |
| 5,846,206 A | | 12/1998 | Bader |
| 5,860,918 A | | 1/1999 | Schradi et al. |
| 5,917,414 A | | 6/1999 | Oppelt et al. |
| 5,942,979 A | | 8/1999 | Luppino |
| 5,989,193 A | | 11/1999 | Sullivan |
| 6,011,477 A | | 1/2000 | Teodorescu et al. |
| 6,014,346 A | | 1/2000 | Malone |
| 6,014,602 A | | 1/2000 | Kithil et al. |
| 6,047,203 A | | 4/2000 | Sackner et al. |
| 6,050,940 A | | 4/2000 | Braun et al. |
| 6,146,332 A | | 11/2000 | Pinsonneault et al. |
| 6,160,478 A | | 12/2000 | Jacobsen et al. |
| 6,195,008 B1 | | 2/2001 | Bader |
| 6,198,394 B1 | | 3/2001 | Jacobsen et al. |
| 6,224,549 B1 | | 5/2001 | Drongelen |
| 6,248,064 B1 | | 6/2001 | Gopinathan et al. |
| 6,261,237 B1 | | 7/2001 | Swanson et al. |
| 6,280,392 B1 | | 8/2001 | Yoshimi et al. |
| 6,297,738 B1 | | 10/2001 | Newham |
| 6,307,476 B1 | | 10/2001 | Smith et al. |
| 6,315,719 B1 | | 11/2001 | Rode et al. |
| 6,364,834 B1 | | 4/2002 | Reuss et al. |
| 6,375,621 B1 | | 4/2002 | Sullivan et al. |
| 6,402,691 B1 | | 6/2002 | Peddicord et al. |
| 6,445,299 B1 | | 9/2002 | Rojas, Jr. |
| 6,450,957 B1 | | 9/2002 | Yoshimi et al. |
| 6,468,234 B1 | | 10/2002 | Van Der Lois et al. |
| 6,491,647 B1 | | 12/2002 | Bridger et al. |
| 6,497,658 B2 | | 12/2002 | Roizen et al. |
| 6,506,153 B1 | | 1/2003 | Littek et al. |
| 6,516,289 B2 | | 2/2003 | David |
| 6,537,214 B1 | | 3/2003 | Hood et al. |
| 6,547,734 B2 | | 4/2003 | Madsen et al. |
| 6,575,902 B1 | | 6/2003 | Burton |
| 6,579,231 B1 | | 6/2003 | Phipps |
| 6,579,242 B2 | | 6/2003 | Bui et al. |
| 6,585,645 B2 | | 7/2003 | Hutchinson |
| 6,611,206 B2 | | 8/2003 | Eshelman et al. |
| 6,616,606 B1 | | 9/2003 | Petersen et al. |
| 6,671,563 B1 | | 12/2003 | Engelson et al. |
| 6,681,003 B2 | | 1/2004 | Linder et al. |
| 6,687,424 B1 | | 2/2004 | Gerdt et al. |
| 6,723,051 B2 | | 4/2004 | Davidson et al. |
| 6,731,989 B2 | | 5/2004 | Engleson et al. |
| 6,734,802 B2 | | 5/2004 | Halleck et al. |
| 6,774,797 B2 | | 8/2004 | Freathy et al. |
| 6,784,797 B2 | | 8/2004 | Smith et al. |
| 6,791,460 B2 | | 9/2004 | Dixon et al. |
| 6,804,656 B1 | | 10/2004 | Rosenfeld et al. |
| 6,809,643 B1 | | 10/2004 | Elrod et al. |
| 6,821,249 B2 | | 11/2004 | Casscells, III et al. |
| 6,822,564 B2 | | 11/2004 | Al-Ali |
| 6,822,571 B2 | | 11/2004 | Conway |
| 6,822,573 B2 | | 11/2004 | Basir et al. |
| 6,847,301 B1 | | 1/2005 | Olson |
| 6,984,207 B1 | | 1/2006 | Sullivan et al. |
| 7,304,580 B2 | | 12/2007 | Sullivan et al. |
| 7,629,890 B2 | | 12/2009 | Sullivan et al. |
| 7,652,581 B2 | | 1/2010 | Gentry et al. |
| 7,654,962 B2 | | 2/2010 | Sullivan |
| 7,656,299 B2 | | 2/2010 | Gentry et al. |
| 7,666,151 B2 | | 2/2010 | Sullivan et al. |
| 7,689,271 B1 | | 3/2010 | Sullivan |
| 8,698,635 B2 | | 4/2014 | Sullivan et al. |
| 2002/0019584 A1 | | 2/2002 | Schulze et al. |
| 2003/0018241 A1 | | 1/2003 | Mannheimer |
| 2003/0092974 A1 | | 5/2003 | Santoso et al. |
| 2003/0095263 A1 | * | 5/2003 | Varshneya ............. A61B 5/113 356/477 |
| 2003/0167391 A1 | | 9/2003 | Al-Ali |
| 2004/0111296 A1 | | 6/2004 | Rosenfeld et al. |
| 2005/0159987 A1 | | 7/2005 | Rosenfeld et al. |
| 2005/0177400 A1 | | 8/2005 | Rosenfeld et al. |
| 2005/0187796 A1 | | 8/2005 | Rosenfeld et al. |
| 2005/0203777 A1 | | 9/2005 | Rosenfeld et al. |

* cited by examiner

| PARAMETER 1 (P1) | PARAMETER 2 (P2) | ALARM | NOTES |
|---|---|---|---|
| A | A OR B OR C OR D OR E | YES | P1 ⇑ (HARD) |
| A OR B OR C OR D OR E | A | YES | P2 ⇑ (HARD) |
| E | A OR B OR C OR D OR E | YES | P1 ⇓ (HARD) |
| A OR B OR C OR D OR E | E | YES | P2 ⇓ (HARD) |
| B | B | YES | P1 ⇑ P2 ⇑ (SOFT) |
| B | C | NO | |
| B | D | YES | P1 ⇑ P2 ⇓ (SOFT) |
| C | B | NO | |
| C | C | NO | |
| C | D | NO | |
| D | B | YES | P1 ⇓ P2 ⇑ (SOFT) |
| D | C | NO | |
| D | D | YES | P1 ⇓ P2 ⇓ (SOFT) |

| |
|---|
| Bed Exit Alert |
| Heart Rate (Hard) High or Low |
| Respiration Rate (Hard) High or Low |
| Unable to Measure (UTM) |
| HR / RR Warning (Soft -All) |
| Coverlet Disconnected |
| Coverlet Failure |
| Nurse Call Disconnected |
| Network Error |
| Printer Unavailable |
| Invalid password |
| Invalid key press |
| Select Patient |
| Stuck Key |
| Event Marked |
| Out of Bed (with permission) |
| System Malfunction |

SYSTEMS AND METHODS FOR MONITORING PHYSIOLOGY WITH UNABLE-TO-MEASURE ALERTS

CROSS-REFERENCES TO RELATED APPLICATIONS

This application is a division of, and claims priority to, U.S. application Ser. No. 14/252,748, filed Apr. 14, 2014, now U.S. Pat. No. 9,275,533, which is a continuation of application Ser. No. 12/617,652, filed Nov. 12, 2009, now U.S. Pat. No. 8,698,635, which is a division of U.S. application Ser. No. 11/624,207, filed Jan. 17, 2007, now U.S. Pat. No. 7,629,890, which is a continuation-in-part of U.S. application Ser. No. 11/004,589, filed Dec. 3, 2004, now U.S. Pat. No. 7,304,580, which claims the benefit of U.S. Provisional Application No. 60/526,612, filed Dec. 4, 2003, the contents of which are incorporated herein by reference in their entirety.

This application incorporates by reference commonly owned U.S. application Ser. No. 09/662,006, now U.S. Pat. No. 6,984,207, and U.S. application Ser. No. 11/624,200, now U.S. Pat. No. 7,656,299, both in their entirety.

FIELD OF THE INVENTION

The present invention relates generally to monitoring systems, and more particularly has reference to intelligent medical vigilance systems used for monitoring patients, automobile drivers, or other persons whose physiological condition may undergo a change signifying a deterioration in condition, a tendency toward drowsiness, or other state that may have important consequences for that person or for others.

BACKGROUND OF THE INVENTION

Medical monitors have been in use for many years. Typically, medical monitors include patient monitors prescribed by a physician in a non-ICU setting.

While typical devices may be suitable for the particular purpose to which they address, they are not as suitable for providing an invisible "safety net" for a patient that will observe and analyze, and, only in the event of a clinically significant negative condition, notify and report the event to the care staff utilizing the hospital's existing nurse call system.

The main problem with conventional medical monitors is they are designed to respond to rapidly changing situations (found, in ICUs) and thus have a high false alarm rate. Outside the intensive care unit, these monitors are not usually connected to a remote alarm, so local alarms sound, disturbing the patient, their family and friends and the workflow of the various clinicians providing care to the patient. Many attempts have been made to make alarms more meaningful.

Another problem is that standard devices require contact directly to the patient's skin or body via cables or wires. This means constraining the patient's movement to prevent disconnecting the sensors and also creates a danger of entanglement or strangulation from the cables. Additionally, these devices are relatively expensive to purchase and somewhat complex to operate, requiring a trained individual to operate properly.

Thus, a need exists for simpler, less expensive and more accurate methods for noninvasive vital sign monitoring of significant negative conditions and reporting these events. This invention addresses these and other needs.

SUMMARY OF THE INVENTION

Briefly, and in general terms, the present invention involves a new and improved intelligent medical vigilance system for providing an invisible "safety net" that observes and analyzes a person's vital signs. Only in the event of a clinically significant negative condition will the device notify and report the event to the person or the care staff of a health care facility, utilizing, for example, a hospital's existing nurse call system. In so doing, the invention extends the vigilance capability and "reach" of the hospital clinical staff so that their resources can be more effectively applied.

The present invention has many of the advantages of the medical monitors mentioned heretofore and many novel features that result in a new intelligent medical vigilance system which is not anticipated, rendered obvious, suggested, or even implied by any of the prior art medical monitors, either alone or in any combination thereof.

In a presently preferred embodiment, by way of example and not necessarily by way of limitation, the invention generally comprises a bedside unit connected to a sensing array (placed under the patient) and to an existing hospital nurse call system via an interface. The sensing array preferably is a non-invasive piezoelectric sensing film or other similar sensing technology, with an array of sensors installed in soft padding under the bottom sheet of the patient's hospital bed. The sensing array is not directly in contact with the skin of the patient. Within the physical bedside unit are a signal processor and an alarm processor that measure the data and evaluate whether a clinically significant event is occurring.

The bedside unit is a wall-mounted unit with a display that becomes active (comes on) when an alarm condition is enabled or on command by the nurse, by touching any key. It has a number of dedicated and softkey buttons and controls for entering information, setting up specific items and interacting with the system.

The sensing array is a thin, piezoelectric film or other similar sensing technology, with an array of sensors sheathed in soft padding that is easily cleaned. It is placed in the patient's bed, under the bottom sheet (and other padding if needed), not directly in contact with the skin of the patient. It can be integrated into the mattress coverlet, if desired. The monitoring system of the present invention may also be used in chairs to monitor the state of relaxation of a subject via heart rate, blood pressure and respiration rates.

The nurse call feature is made up of hardware, software and cabling to connect to a nurse call system already installed in the hospital or care facility. The signal processor is made up of hardware and software that accepts, buffers and converts the sensor array signal from analog to digital format for subsequent processing. The alarm processor uses logic to monitor the parameter trends and determines when a negative condition is occurring. It then actuates the alarm circuitry for local and/or remote alarm. Soft alarms may be used to report adverse trends before an emergency condition arises. All alarms may interact with the existing nurse call system in the hospital.

In alternative embodiments, the intelligent medical vigilance system of the present invention can be adapted for use as a monitoring system for operators of motor vehicles, aircraft or other devices. The present invention is installed in one or more of the following regions of a motor vehicle: the seat, seatback, headrest, steering wheel, driving jacket, or a driving cap. One or more sensors may be located in each general location to provide for improved feedback. The vehicle operator may also carry a wrist attachment or a necklace with built in sensors.

The sensors in the vehicle transmit information about the patient to a central processor built into the vehicle via hardwiring or wireless technology. The processor analyzes the incoming information and outputs data as needed. The vigilance system can be used to alert drivers to approaching sleep states or other potentially hazardous physical conditions in order to reduce accidents. The sensors measure heart rate, respiration rate and movement of the vehicle operator.

Background noise signals are actively cancelled out to provide an accurate reading of the patient's heart rate, respiration rate and blood pressure. This cancellation allows the monitoring system to operate effectively in high background noise environments.

Trend information is also recorded and available for study.

The present invention provides an intelligent medical vigilance system that overcomes many of the shortcomings of the prior art devices.

In a preferred embodiment, the present invention provides an intelligent medical vigilance system for providing an invisible "safety net" for the patient that will observe and analyze, and, only in the event of a clinically significant negative condition, notify and report the event to the care staff utilizing the hospital's existing nurse call system.

In a further preferred embodiment, the invention provides an intelligent medical vigilance system that observes (monitors) multiple physiological signals without direct skin contact.

In yet a further embodiment, the invention provides an intelligent medical vigilance system that analyzes the information to determine whether the parameters are within normal limits or are tending to go in a clinically negative direction.

In a further aspect, the invention provides an intelligent medical vigilance system that reports the physiological parameters and provides a trend of them over time.

In yet a further aspect, the invention provides an intelligent medical vigilance system that notifies the nursing care staff when a consistently negative situation is detected via the existing nurse call system used in the facility.

In still a further aspect, the invention provides an intelligent medical vigilance system that persistently reminds nursing of continued violations or worsening situation until interventions are successful. This aspect provides an intelligent medical vigilance system that extends the vigilance capability and "reach" of the busy clinical staff so they can spend time where it has the best clinical effect.

In another aspect, the invention provides a sensor system within vehicles that alerts operators to dangerous physiological conditions that would impair the operator's ability to operate equipment safely.

These and other advantages of the invention will become more apparent from the following detailed description, taken in conjunction with the accompanying drawings, which illustrate, by way of example, the features of the invention.

DETAILED DESCRIPTION OF THE PREFERRED EMBODIMENTS

Figure 1:
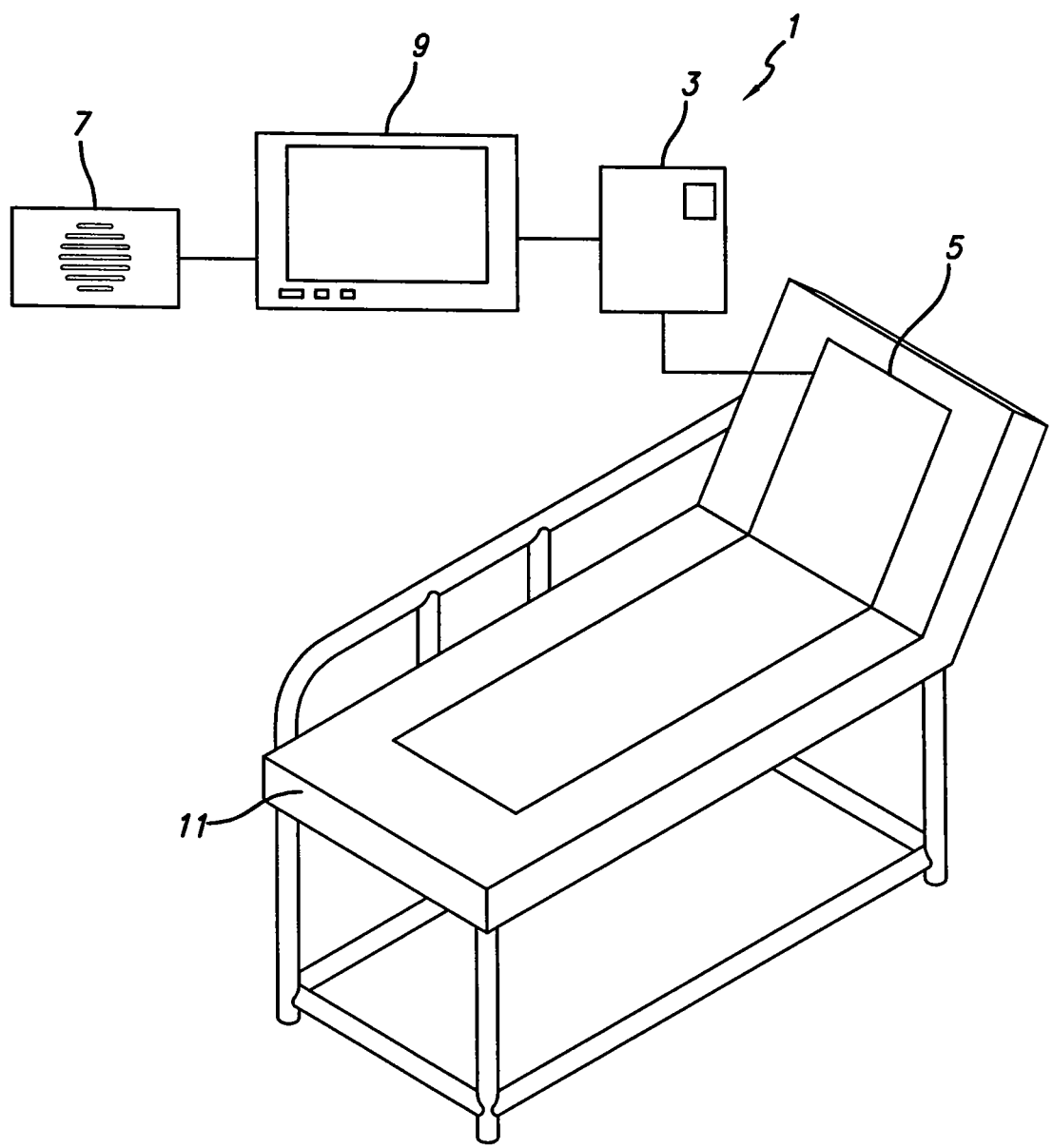
FIG. 1 is a diagram of the vigilance monitoring system of the present invention.

FIG. 1 illustrates an intelligent medical vigilance system 1, which comprises a bedside unit 3 connected to a sensing array 5 (placed under the patient) and also to an existing hospital call system 7 via an interface 9. Within the physical bedside unit 3 are a signal processor and an alarm processor that measure the data and evaluate whether a clinically significant event is occurring. The present invention can also be used as a monitoring system in vehicles.

The bedside unit 3 is a wall-mounted unit with a display 9 that becomes active (comes on) when an alarm condition is enabled or on command by the nurse, by touching any key. It has a number of dedicated and softkey buttons and controls for entering information, setting up specific items and interacting with the system.

While various types of sensors can be used, it is preferred that the sensing array 5 be in the form of a thin, piezoelectric film sensing array sheathed in soft padding that is easily cleaned. It is placed in the patient's bed 11, under the bottom sheet (and other padding if needed), not directly in contact with the skin of the patient. The sensing array 5 may be incorporated into soft padding under the bottom sheet of a patient's bed.

The nurse call feature 7 is made up of hardware, software and cabling to connect to the nurse call system already installed in the hospital or care facility.

The signal processor is made up of hardware and software that accepts, buffers and converts the sensor array signal from analog to digital format for subsequent processing. Trend information is recorded and available for study.

The alarm processor uses logic to monitor the parameter trends and determines when a negative condition is occurring. It then actuates the alarm circuitry for local and/or remote alarm. Soft alarms may be utilized to report adverse trends before emergency situation arises.

Figure 2:
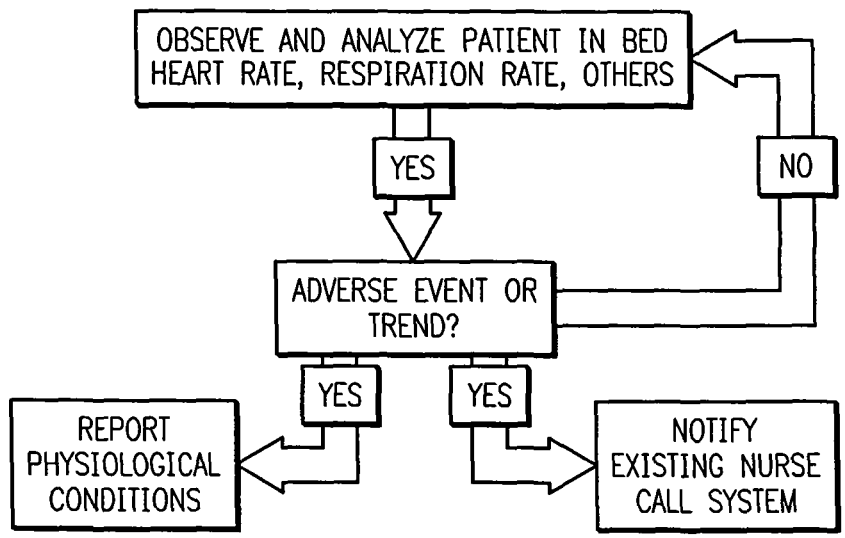
FIG. 2 is a block diagram of the system functions.
Figure 3:
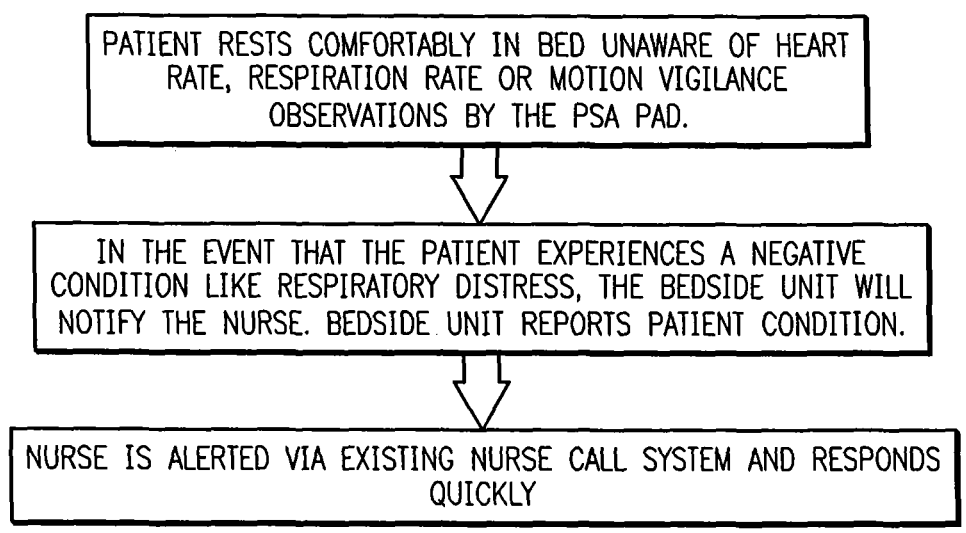
FIG. 3 is a diagram showing progression from normal patient condition to negative event and nurse response.

FIG. 2 shows a schematic diagram of the monitoring process of the present invention. FIG. 3 is a diagram showing progression from normal patient condition to negative event and nurse response.

In all patient monitoring devices with alarms the user can set "hard" alarm limits—those high and low single-parameter limits that, when passed, will cause the alarm indication, signal and tone to be transmitted to the caregiver by any number of means. The caregiver responds to correct the situation. One problem caused by such alarms is that of false positive alarms—those alarms that sound because the set threshold is passed momentarily, but that are not associated with a clinically significant event. In order to monitor the patient closely the alarm limits may be set close to the patient's present parameter value. The closer these are set, the more likely it is that a minor actual parameter variation, patient movement or other signal "noise" will make the measured parameter surpass the set alarm limit.

Few if any alarms use any delay or additional processing other that the filtering used to compute the average of and display the parameter's value. There have been many attempts to measure the inadequacy of such simple alarms in the intensive care unit. There are also methodologies used to delay alarming until a certain time since passage outside the range integrated with the extent of the deviation beyond the set range is exceeded.

In an intelligent vigilance monitor such as the one used in this invention, the "hard" alarm limits can be spread more widely than in conventional intensive care unit monitors. This is done because the patients being monitored may be relatively healthy and mobile compared to typical ICU patients. Because of their high activity level they exhibit a lot of variability in their measured vital parameters such as heart rate, respiratory rate, blood pressure, temperature, cardiac activity, etc. Thus, the clinician wants to watch over these patients' condition, but also wants to avoid false positive alarms that disrupt the patient care workflow and the feelings and outlook of the patient. However, the clinician is still interested in detecting negative trends in the patient so they can react quickly to treat or avoid deeper, more serious problems.

Figures 4, 5:
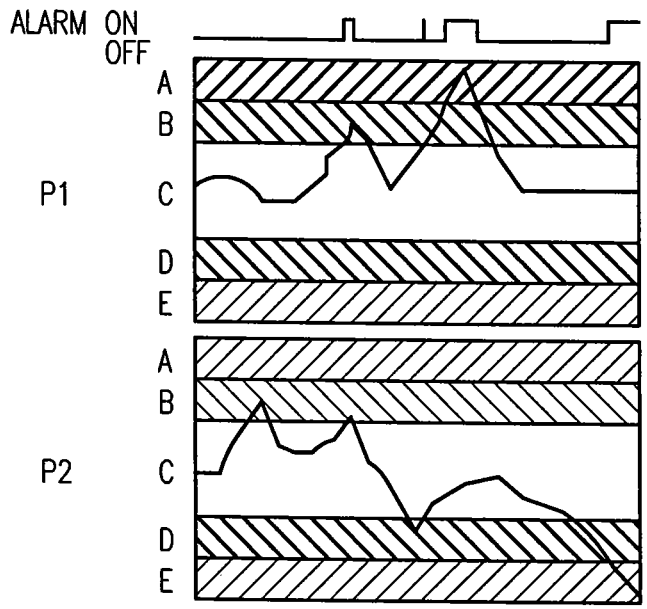
FIG. 4 is a time plot of multiple parameters, showing various parameter violations and alarm logic.
FIG. 5 is multiple parameter alarm table, showing alarm logic.

FIGS. 4 and 5 show the use of alarm limit pairs and algorithms. FIG. 4 is a time plot of multiple parameters, showing various parameter violations and alarm logic. FIG. 5 is multiple parameter alarm table, showing alarm logic.

To accomplish a balanced response, the monitor of the present invention has two or more distinct alarm limit pairs and algorithms. The purpose of the new alarm scheme is to set new thresholds within the previous "hard" limits of each parameter that will catch a patient's worsening condition prior to crossing the old single "hard" limits. This differs from just moving those limits in because these new, soft limits require that both the HR and RR values (in this example) be outside the soft limits to initiate the alarm. If either the HR or RR falls outside a hard limit, then the alarm sounds. If both the HR and RR fall outside the soft limit, but still within the hard limit, then the "soft" alarm sounds. This is best described in FIG. 4.

The parameters covered by such an alarm scheme are not limited to Heart Rate and Respiratory Rate, used in this example. In fact non-parameter-based signals (noise, motion etc.) can also be included in this logic scheme to make it more clinically valuable. In addition, the sensitivity and specificity of the "hard" alarm may be improved by using a more-complex algorithm than just "did it pass the limit?" used in many systems. This improvement could take the form of applying a number of approaches including but not limited to neural net and/or fuzzy logic.

Fuzzy logic could be applied to the limit as follows: Given one or more measurements of physiological parameters (e.g. heart rate, respiration rate, blood pressure, temperature, etc.) which require an alarm when the measurement is outside of a range (or band), a fuzzy logic type function can be defined as follows:

$$A = \sum_{n=0}^{N-1} F_n(p_n),$$

an alarm truth function, based on N different parameters or signals, and a signal truth function $F(p)$ for each parameter or signal $$F(p) = \begin{cases} 1, \text{ for } p < t_{L1} \\ > 0 \text{ for } t_{L1} \leq p \leq t_{Lh} \\ 0, \text{ for } T_{Lh} < p < t_{H1} \\ > 0, \text{ for } t_{H1} \leq p \leq t_{Hh} \\ 1, \text{ for } p > t_{Hh} \end{cases},$$

with the additional constraint that $F(p)$ must be monotonically increasing for $t_{Hl} <= p <= t_{Hh}$ and monotonically decreasing for $t_{Ll} <= p <= t_{Lh}$.

The sum of N different physiological fuzzy logic functions can be used to establish an alarm equation (See alarm truth function above) described further as follows: When $A >= Ta$, the alarm sounds, otherwise it does not. Ta is typically set to 0.5 if any weak (or soft) condition (or combination of weak conditions) is to cause an alarm. If Ta is set to 1.0 a strong alarm condition from at least one physiological parameter is required for the alarm to sound. If it is desired that the alarm only sound when Physiological parameters are at or above $t_{Hh}(n)$ (or below $t_{Ll}(n)$), then Ta can be set to N. This method can also be used when the same physiological parameter is measured by multiple means.

In the case of two measurements of the same physiological parameter, the $F(p)$ functions would most likely be the same for each measurement and Ta could be set to 1.0 such that if either device exceeded the $t_H$ limits, the alarm would sound. The alarm violation type (hard, soft, etc.) may be differentiated from each other or not, depending on the needs for the specific clinical application (ICU versus General Care Floor, etc.). The alarms may be set individually for each parameter as soft high and soft low or may be set by using a fixed percentage, such as 10% within the range of the hard limits for each parameter. The logic can also be extended to more than two alarms if needed.

The sensitivity of both the "hard" and "soft" limits also may be improved by delaying the alarm until the monitor determines that a signal has passed a limit for a certain length of time, such as 10 seconds. In this way, momentary changes in a signal having no clinical significance can be ignored.

Figure 6:
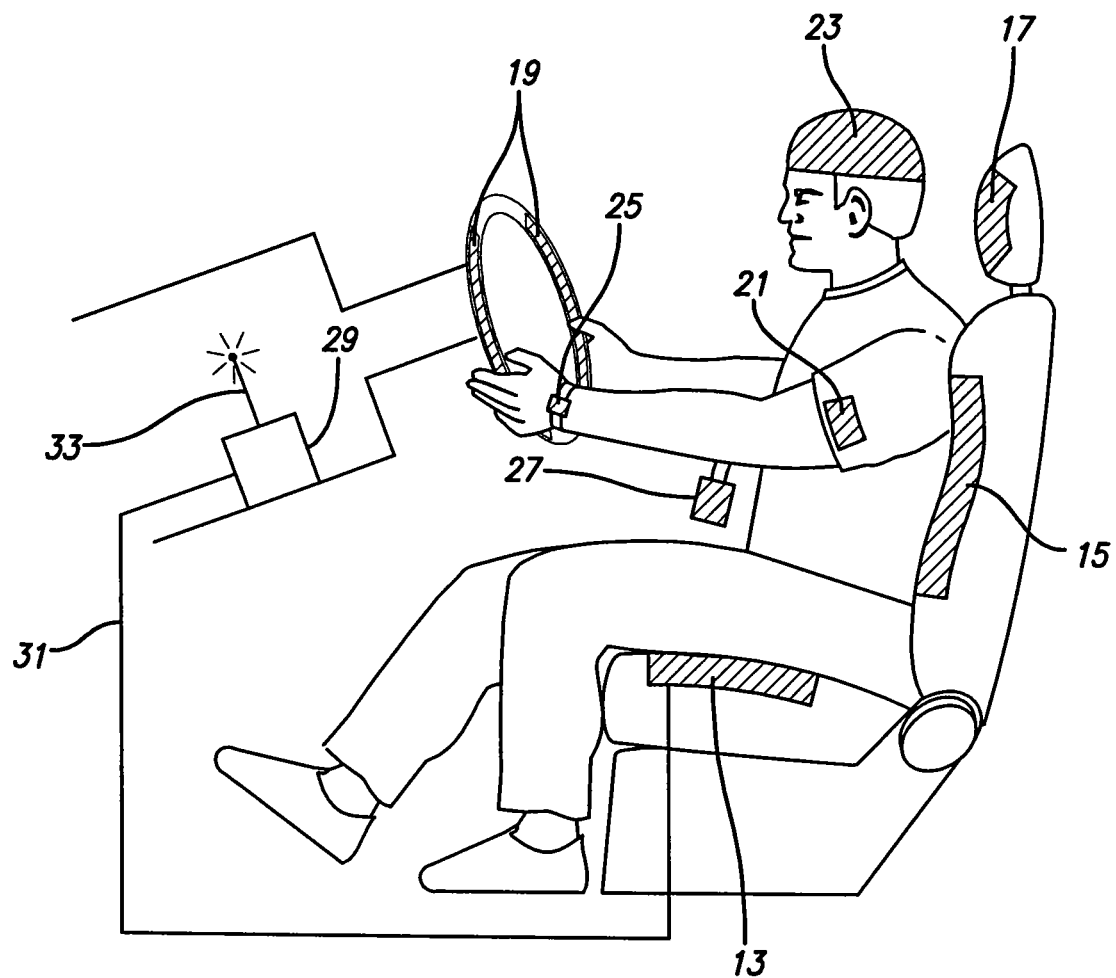
FIG. 6 is a diagram showing various configurations of sensors in a vehicle.

FIG. 6 is a diagram of the present invention installed in a vehicle. The intelligent medical vigilance system of the present invention can easily be adapted for use as a monitoring system for operators of motor vehicles, aircraft or other devices. The sensing array of the present invention is installed in one or more of the following regions of a motor vehicle: the seat 13, seatback 15, headrest 17, steering wheel 19, driving jacket 21, or a driving cap 23. One or more sensor arrays may be located in each general location to provide for improved feedback. The vehicle operator may also carry a wrist attachment 25 or a necklace 27 with built in sensor arrays.

The sensor arrays in the vehicle transmit information about the patient to a central processor 29 built into the vehicle via hardwiring 31 or wireless 33 technologies. The processor analyzes the incoming information and outputs data as needed. The vigilance system can be use to alert drivers to approaching sleep states or other potentially hazardous physical conditions in order to reduce accidents. The sensors can be configured to measure a variety of parameters, such as heart rate, respiration rate, blood pressure, temperature, cardiac output and movement of the vehicle operator. The intelligent monitoring system in vehicles uses similar alarm schemes to those in a hospital setting.

Background noise signals are actively cancelled out to provide an accurate reading of the operator's measured physiological parameters. This cancellation allows the monitoring system to operate effectively in high background noise environments.

There are various ways to enhance the reliability of the vigilance system, and make it even more useful as a tool for improving patient care and clinical operations in a hospital, nursing home, assisted living facility or other health care facility.

In one approach, a bed exit detection system can be integrated into the physiological parameter monitoring system and used to ensure that the vigilance (parameter) alarms (alerts) will be discontinued once a patient leaves his bed and will remain suspended until the patient returns to bed. In this way, the occurrence of a false alarm due to an empty bed, rather than an actual physiological condition of the patient, will be reduced.

Bed exit detection systems of various kinds are known. A bed exit detection system continually monitors the presence or absence of a patient to determine whether the patient is in bed, is out of bed, or is attempting to exit the bed. These systems generally include some form of sensing device attached to the bed, and a processor which is programmed to analyze signals from the sensor device to determine the patient's bed status and provide an alarm indication when out-of-bed, or often when an exiting-bed condition, is detected. A bed exit detection system which is especially well suited for use with the present invention is described in a commonly assigned, co-pending patent application entitled "Bed Exit and Patient Detection System" by Gentry, Glei, and Mills, filed concurrently herewith, the full disclosure of which is incorporated herein by reference. The system described in the co-pending application is especially well-suited because it provides both accurate in-bed and out-of-bed detection capabilities and because it can be easily integrated into a physiological monitoring system of the type described herein.

The bed exit alarm is preferably made non-latching, i.e. if the patient exits the bed or tries to exit the bed the alarm will sound (if set), but if the patient responds to the alarm and gets back into bed, the alarm is silenced and reset. In some systems, the alarm includes a pre-recorded voice message played in the vicinity of the patient's bed warning the patient to return to the bed.

Figure 7:
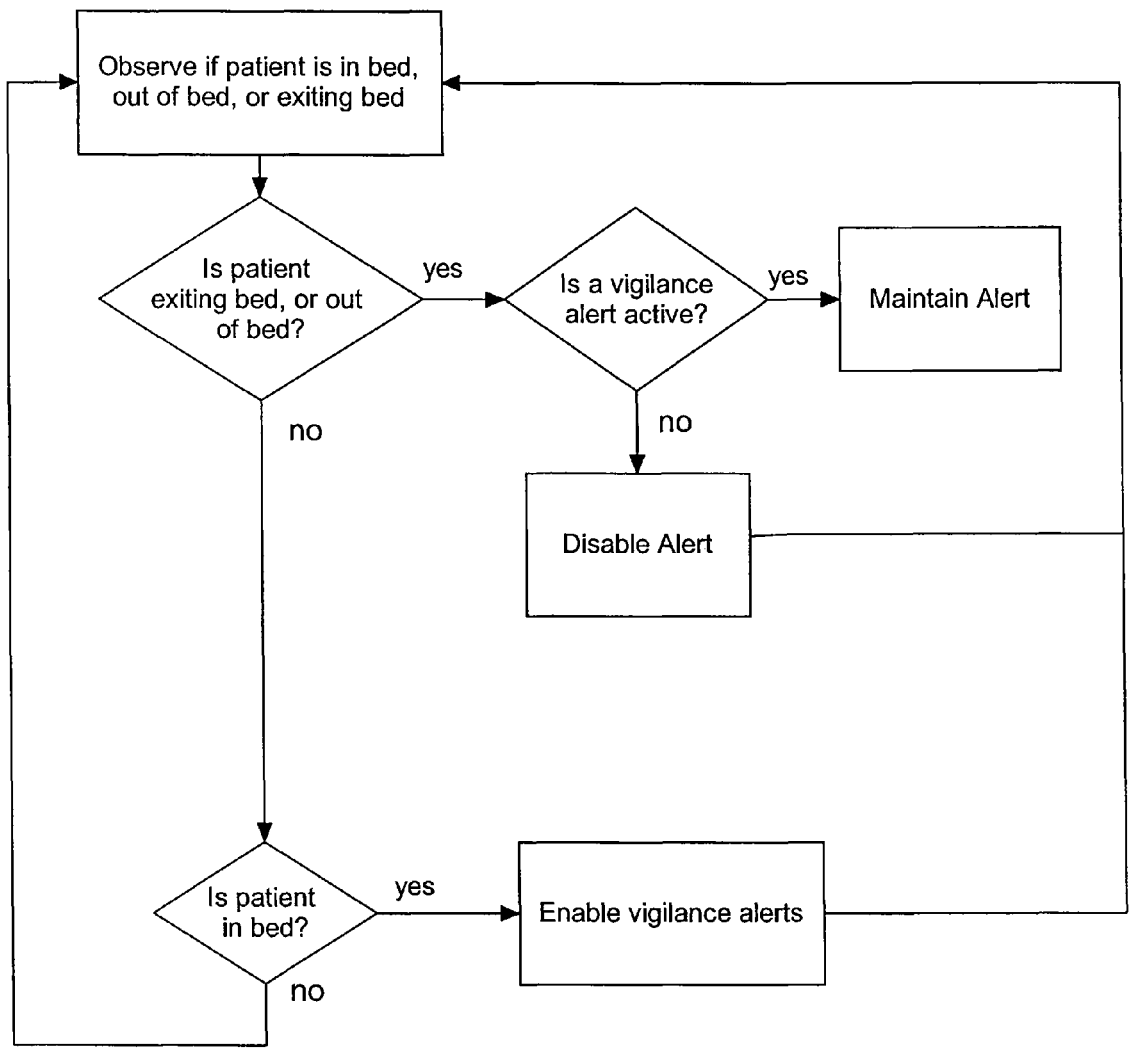
FIG. 7 is a flow diagram illustrating one embodiment of using a bed exit detection system to enable and disable patient parameter alarms.

The bed exit system can be utilized with the physiological parameter monitoring system in at least two ways, as shown in FIG. 7. First, if there are no active vigilance alarms before the patient exits the bed or tries to exit the bed, the vigilance alarms are suspended until the patient is detected back into bed. Once the patient leaves the bed, no new vigilance alarms are generated.

On the other hand, if a vigilance alarm is active before the patient leaves the bed or tries to leave the bed, those alarms are continued even after the patient leaves the bed. The alarms are continued to inform the nurse or clinical staff of the patient's condition before the bed exit event occurred.

In the present invention, the bed exit detection system can be integrated with the physiological parameter monitoring system in several different ways, but in at least one approach, the patient parameter sensors and the bed exit sensors are mounted in a common sensing array 5, and both the bed exit detection function and the physiological monitoring function are carried out by the same processors, which are programmed to disable the vigilance alarms when an out-of-bed or an exiting-bed condition is detected, and to enable the vigilance alarms when an in-bed condition is detected. In most cases, it is desirable to continue physiological monitoring and data collection even when the vigilance alarms are disabled, so that the data may be stored in memory for future review and analysis, as needed. In addition, in most cases, the arming and disarming of the vigilance alarms will continue, even if the bed exit alarm is turned off, as for example, in the case of a patient who is not on bed exit restrictions.

It will be appreciated that a bed exit detection system can be integrated with any type of physiological parameter monitoring system in the manner described, and that the invention is not limited to the particular parameter monitoring and alarm system described herein.

In some embodiments, it also may be desirable to alert the nurse or other caregiver that the system is unable to reliably monitor the patient due the presence of certain extenuating conditions. The conditions which might result in an unable-to-measure (UTM) situation are generally predetermined, and can differ from system to system. Examples of typical UTM conditions might include (1) excessive patient motion such as that caused by seizures, physical or chest therapy, or the application of certain devices that may cause severe motion (large enough to cause the sensor signal-to-noise ratio to fall below a predetermined threshold); (2) low or no signal from the physiological sensors (e.g. sensor signal falls below the noise threshold of the system or below a predetermined amplitude threshold); (3) a foreign object (e.g. a heavy suitcase) being placed on the bed surface (resulting in an in-bed determination by the bed exit detection system, but no physical signal from the physiological parameter sensors); (4) a "Select Patient" prompt not being answered by the clinician during initial set up of the system to start monitoring for a new patient; (5) sensor disconnection or sensor failure; (6) heart rate (HR) above or below operational limits of the system (for example, 35-200 beats per minute); or (7) respiration rate (RR) above operational limits of the system (for example, 70 breaths per minute). If any of these conditions persist for a prescribed delay period (e.g. two minutes or more), an alarm will be generated to bring someone to the patient's bedside. A two minute threshold for the delay time provides a balance between speed of response and the occurrence of false alarms. A shorter delay time threshold would provide a faster response but a higher probability of false alarms. A longer delay time threshold, on the other hand, would reduce the occurrence of false alarms but might not provide enough time for a response team or nurse to administer treatment to a patient undergoing seizures or to otherwise resolve in a timely fashion the condition which caused the UTM alert.

Figure 8:
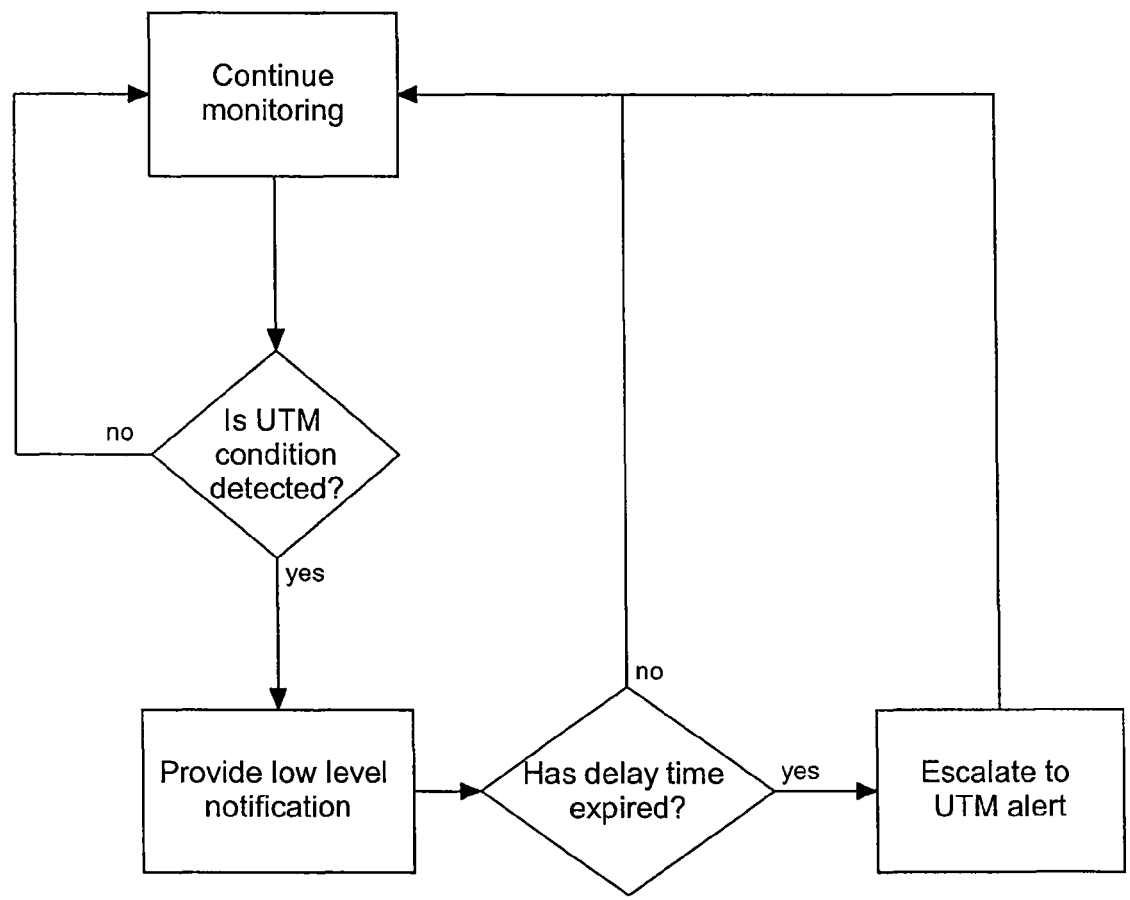
FIG. 8 is a flow diagram illustrating one embodiment of a system with an unable-to-measure alert capability.

In some embodiments, as shown for example in FIG. 8, a UTM condition initially is reported as a low level notification to the caregiver on the display screen 9 when the condition is first detected by the processor, then escalated to a full UTM alert if the condition persists for the preset delay time, in order to notify the caregiver that a patient is not being monitored. A typical UTM indication on the display screen 9 would include a dash/dash (--) display for heart rate and respiration rate. While the UTM condition is non-latching (low level notification is non-latching), the escalated UTM alert is a latching alert. In other words, if the UTM condition persists for less than the delay period (e.g., two minutes) and then resolves itself, the low level notification is removed from the screen and no UTM alert is initiated. However, once the full UTM alert is triggered after the delay period, it will continue, even if the UTM condition resolves itself.

Figure 9:
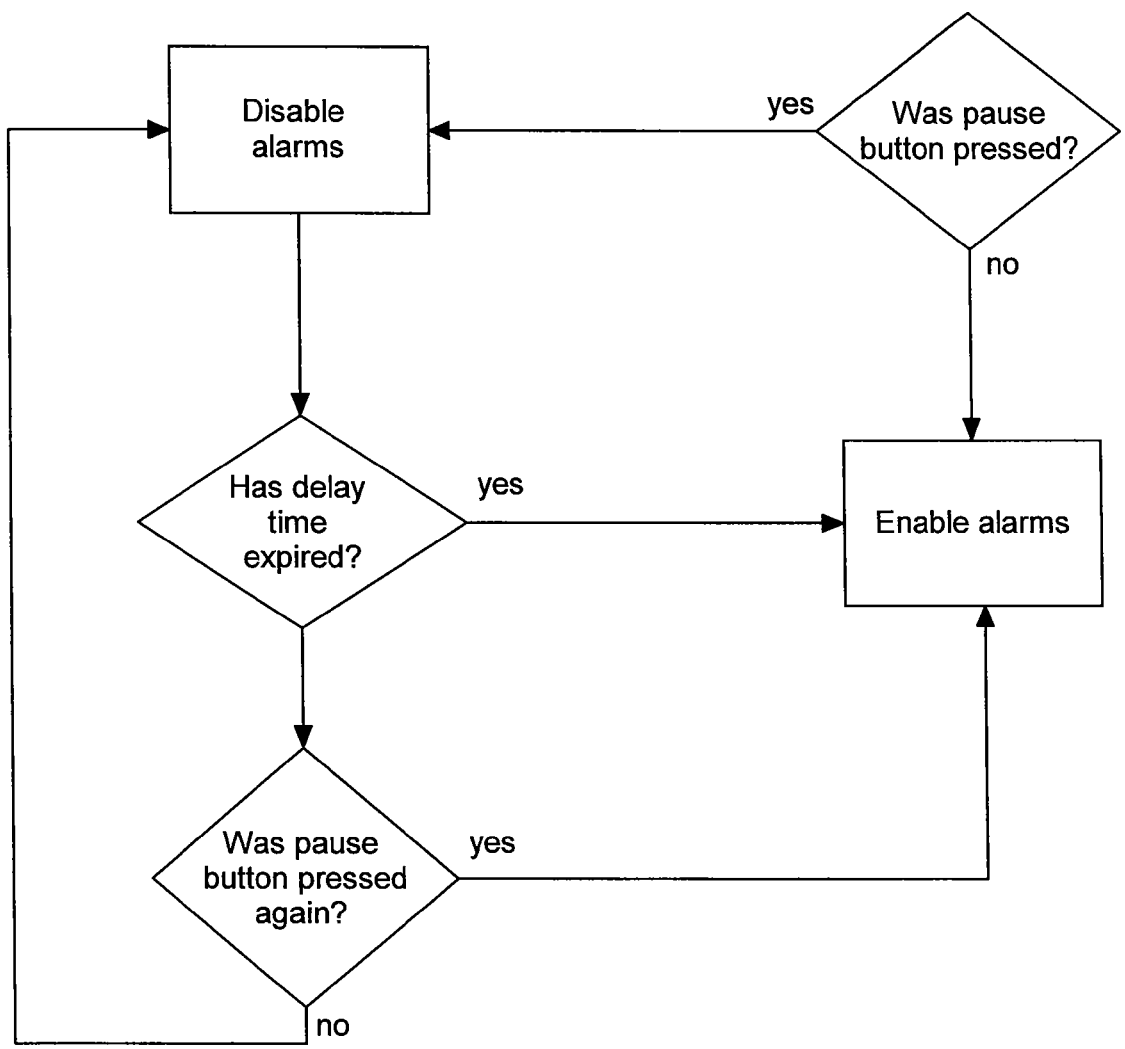
FIG. 9 is a flow diagram illustrating one embodiment of an alarm pause function.

Another approach for improving the vigilance system, involves providing an Alarm Pause function as shown in FIG. 9, which causes both the parameter alarms and the bed exit alarms to be paused for a period of time (such as, for example, five minutes). In the case of the parameter alarms, the alarm pause function will temporary silence any audible alarm and reset the nurse call relay to its normal state to give the responding caregiver time to investigate and resolve the situation causing the alarm. In at least one embodiment, the alarm pause function is actuated by a push button which starts a timer counting down from the preset delay time (e.g., 300 seconds) and automatically re-enables the alarm once the alarm pause period times out. If the condition causing the alarm remains in effect, the alarm signal is re-initiated. If the responding caregiver wishes to re-enable the alarm before the alarm pause function has timed out, they can press the alarm pause button again and the alarm will be re-enabled. On the other hand, if they press the alarm pause button a third time, i.e. after the alarms are re-enabled, they will place the unit into alarm pause mode again for another preset period of time.

In the case of the bed exit alarms, the alarm pause button is typically pressed when the nurse or other caregiver wants to remove a bed restricted patient from the bed or to perform some procedure which may interfere with bed exit monitoring. The reason for the bed exit alarm is to alert the nurse or caregiver to abnormal conditions. Thus, if the patient is being assisted by the nurse, there is no reason to initiate or continue a bed exit alarm. Instead of asking the caregiver to change the bed exit restriction setting (on/off) every time the patient is helped out of the bed for bathroom visits and the like, the alarm pause function is used to provide a form of supervised bed exit. Supervised bed exit is activated if the patient leaves the bed when alarm pause is active or if alarm pause is pressed after the patient has left the bed. With supervised bed exit, the nurse or caregiver can suspend the bed exit alarm when the patient leaves the bed with assistance, and automatically re-enable the bed exit alarm once the patient returns to the bed.

In most cases, the alarm pause function is provided by the microprocessor in the bedside unit 3 which is programmed to sense the input signals from the sensing array 5 and, in response and in accordance with its programming instructions, to generate an output signal for activating the alarms. In at least one embodiment, the processor is configured to receive user instructions via an external signal from a push button 12 mounted on the face of the bedside unit housing. By pressing the button 12, the caregiver instructs the program to enter into the alarm pause mode, causing the processor to discontinue any current alarms and to wait for the preset period of time before generating an output signal to the alarm circuit or the nurse call system 7. Pressing the button a second time instructs the processor to override the time delay.

In addition to reporting the occurrence of a clinically significant negative condition to the care staff by sending an alarm signal over the nurse call system 7 and/or by generating a local alarm at the bedside unit 3, in at least some embodiments, the system also is configured to display an alert message on the bedside unit display screen 9 informing the caregiver of the type of alert, the values that triggered the alert, and the time the alert was raised. In this way, a caregiver responding to an alarm over the nurse call system will be informed immediately upon entering the patient's room why and when the alarm was raised, so that he or she can begin to immediately resolve the problem or situation.

The alert messaging system can be configured in a variety of different ways, but in at least one embodiment, the alert messaging system is configured to display at least four messages in a priority-based queue with the four highest priority messages being displayed at any given time. The messages can be further divided into two types, latching alert messages and non-latching alert messages. A latching alert is one that remains in an alarm condition once the alarm signal is initiated until stopped by a deliberate action on the part of a responder. A single queue is provided for both latching and non-latching messages, with a maximum of four messages being displayed at any time. If the queue is longer than four, there will be queued messages that are not currently on display.

A latching alert message typically accompanies latching physiological alarms. Thus, for example, the heart rate and respiration rate values that caused the alarms and the time at which the alarms was raised are part of the message. The messages are cleared only when the alarm is cleared or reset. Clearing a latching alert message requires user intervention. If multiple latching alarms of the same type occur while an alarm is active, the message accompanying the first instance of the alarm will continue to be displayed.

One of the benefits of a latching alert message is that it provides the responding caregiver with an immediate indication of the reasons for an alarm regardless of how long ago the alarm event occurred. Traditional monitors typically display information concerning the current state of the patient, which might return to normal by the time a caregiver responds to an alarm. In such cases, the caregiver will not immediately know the reason for the alarm, and might mistakenly believe that a false alarm has occurred. By providing a latching alert message in accordance with the present invention, the caregiver is immediately informed of the reason for the alarm as soon as they reach the patient's bedside.

Non-latching alert messages typically accompany non-latching bed exit alerts (in systems equipped with a bed exit detection capability). The type of alert and the time at which the alert was raised are part of the message. The message is cleared only when the alert is cleared. Thus, if the condition that caused the alert is resolved (such as by the patient returning to bed), the alert is reset. However, the alert message continues to be displayed even if the alert is reset until user intervention. If multiple alerts of the same type occur, then multiple messages are generated and displayed according to the assigned priorities.

Figures 10, 11:
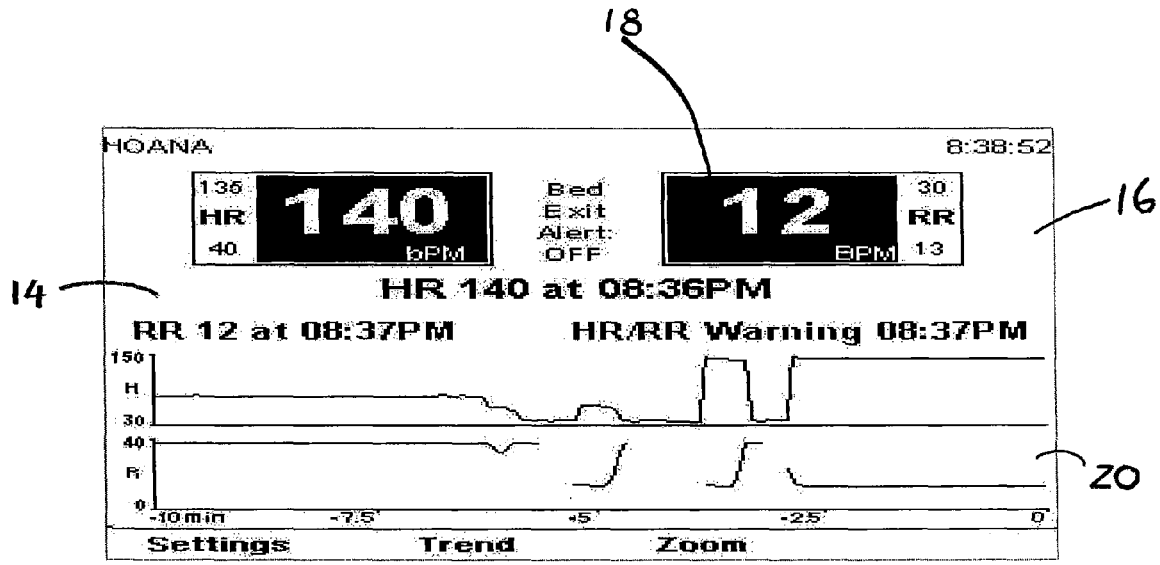
FIG. 10 is an enlarged illustration of a screen display for the display device of FIG. 1, showing alert messages.
FIG. 11 is a table showing a set of alert message priorities.

FIG. 10 is an example of a typical screen display produced by the bedside unit 3 on the display monitor 9. A message box area 14 is provided between a parameter display area 16 at the top of the screen (containing numeric windows 18 for heart rate and respiration rate) and a trend and waveform area 20 at the bottom of the screen (containing waveform and trend displays for the heart rate and respiratory rate data). The message box window 14 is used to display the alert messages to the caregiver. In the embodiment shown, three alert messages are displayed simultaneously. The first message shows that a heart rate of 140 bPM (exceeding the upper heart rate limit of 135 bPM for that patient) occurred at 8:36 P.M. The second message shows that a respiration rate of 12 BPM (below the 13 BPM lower limit for the patient) occurred at 8:37 P.M. The third message shows that a soft limit HR/RR warning also occurred at 8:37 P.M. All three messages are displayed simultaneously in priority order.

In the embodiment shown, up to four short messages can be displayed in the message box 14 to indicate the reason for any alarm, or to provide other alert message. It will be appreciated, however, that the size, location and/or capacity of the message box can be varied, if desired. When an alert message comes up, a beep tone typically will sound from the bedside unit 3 to signal the caregiver that there is a new message. The message is cleared by the caregiver by pressing the alarm pause button 12.

While various different priority assignments can be made, a typical set of priority assignments for use with the present invention is shown in FIG. 11. In this example, the bed exit alerts are given the highest priority, followed by the heart rate (hard limits), respiration rate (hard limits), unable-to-measure (UTM), and HR/RR warnings (soft limits), in that order. The remaining (lower) priorities in this example are assigned to various mechanical failures and system malfunctions. It will be appreciated that fewer or more priority items can be used, and that the order of priorities rearranged, if desired.

Figure 12:
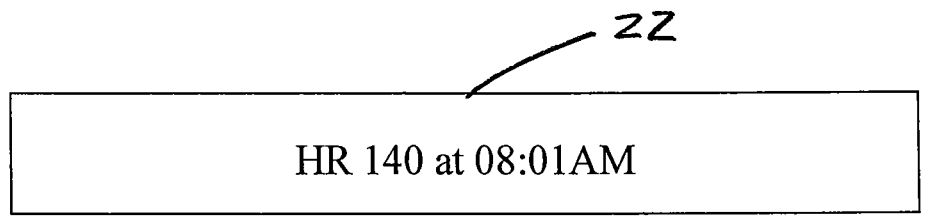
FIG. 12 is an enlarged illustration of a latching alert message for the screen display of FIG. 10.

The operation of the latching alert messages can be best understood by reference to FIG. 12. Assume, for example, a patient with a heart rate (HR) hard limit of 130 bPM (upper) and 40 bPM (lower). If the patient's heart rate rises to 140 bPM at 8:01 A.M., an alert is raised. The nurse call light is turned on, and the display screen on the bedside unit displays an alert message 22 of the type shown in FIG. 12. If the patient's heart rate falls to 110 bPM at 8:02 A.M., the nurse call light remains on, and the same alarm message 22 remains on the screen. If the patient's heart rate rises to 150 bPM at 8:03 A.M., the nurse call light continues to be on and a new alert is raised, but the same alert message 22 remains on the display screen, as shown in FIG. 12. The alert message remains unchanged because the new alert is of the same type (i.e. HR hard limit) as the initial alert, and in such cases, the initial alert message remains on the display 9. If the patient's heart rate subsequently falls to 110 bPM at 8:06 A.M., the alert message 22 on the display 9 will continue to remain unchanged, until the nurse visits the patient's room and presses the alarm pause button 12 or otherwise resets the system. Pressing the alarm pause button turns off the nurse call light and clears the alert message from the screen. Thus, it will be appreciated, that a latching alert message remains on the screen until both the alert condition goes away and the alarm pause button 12 is pressed (or the system is reset by the caregiver in some other fashion).

Figure 13A:
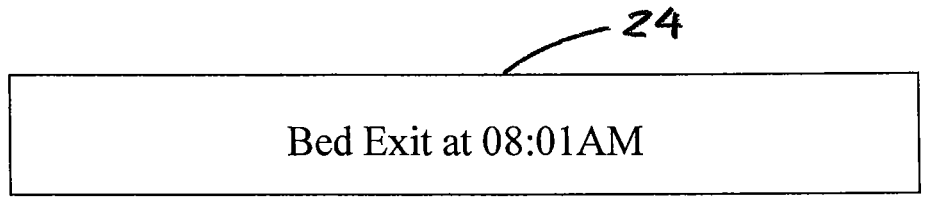
FIGS. 13A and 13B are enlarged illustrations of non-latching alert messages for the screen display of FIG. 10.
Figure 13B:
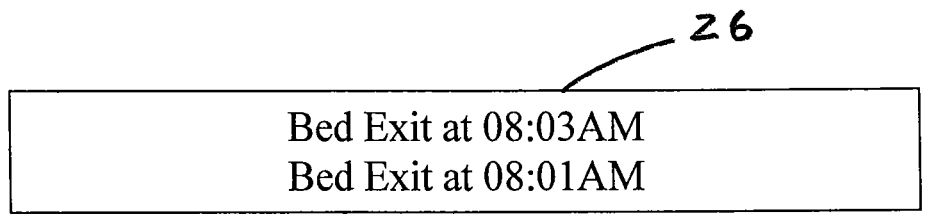

Operation of the non-latching alert messages is best understood by reference to FIGS. 13A and 13B. Assume a patient on bed exit restrictions with the bed exit alarm system turned on. If the patient leaves or tries to leave the bed at 8:01 A.M., a bed exit alert is raised, the nurse call light is turned on, and an alert message 24 is displayed on the screen 9 of the type shown in FIG. 13A. If the patient returns to bed at 8:02 A.M., the bed exit alert is discontinued, the nurse call light is turned off, but the message 24 remains on the screen 9. If the patient leaves the bed again at 8:03 A.M., the nurse call light is once again turned on, and the alert message 26 now reports both alarm occurrences in chronological sequence from top (most recent) to bottom (less recent), as shown in FIG. 13B. Both alert messages will remain on the screen until the alarm pause button 12 is pressed or the system is otherwise reset by the caregiver.

While particular forms of the invention have been illustrated and described, it will also be apparent to those skilled in the art that various modifications can be made without departing from the spirit and scope of the invention. Accordingly, it is not intended that the invention be limited except by the appended claims.

We claim:

1. A method for improving the reliability of a system for monitoring physiology of a person, comprising:
   placing adjacent the person a plurality of sensors configured to detect physiological parameters of the person;
   detecting one or more physiological parameters of the person with said sensors;
   converting the detected parameters to signals;
   assigning one or more alert conditions;
   analyzing the signals to determine if they satisfy at least one of the alert conditions;
   activating an alert when at least one of the signals satisfies an alert condition;
   assigning one or more unable-to-measure conditions which indicate that at least some of the signals are unreliable;
   analyzing the signals to determine if they satisfy at least one of the unable-to-measure conditions; and
   providing an unable-to-measure alert when at least one of the unable-to-measure conditions is satisfied.

2. The method of claim 1, wherein the unable-to-measure conditions are selected from a group consisting of excessive motion by the person, low signal amplitude, low signal-to-noise ratio, sensor disconnection, sensor failure, and patient parameters outside operational limit.

3. The method of claim 2, further comprising:
   placing a plurality of sensors on a bed to detect a presence thereon of a person or a foreign object;
   detecting or more signals from said sensors on the bed; and
   analyzing the signals to determine whether a person or foreign object is in the bed;
   wherein the unable-to-measure conditions further comprise the presence of an in-bed determination with the absence of a signal from the sensors configured to detect physiological parameters.

4. The method of claim 3, further comprising;
   activating a bed exit alert when the signals from the sensors on the bed indicate that the person is out of bed; and
   disabling the bed exit alert when the person is removed from the bed under supervision.

5. The method of claim 1, wherein the unable-to-measure alert is provided only when the at least one unable-to-measure condition persists for a predetermined minimum period of time.

6. The method of claim 5, wherein the unable-to-measure alert comprises an alarm.

7. The method of claim 5, wherein a low level notification is provided when the at least one unable-to-measure condition persists for less than the predetermined minimum period of time.

8. The method of claim 7, wherein the low level notification comprises a sequence of dashes on a display screen.

9. The method of claim 5, wherein the unable-to-measure alert is a latching alert.

10. The method of claim 7, wherein the low level notification is non-latching.

11. The method of claim 1, wherein the unable-to-measure alert comprises a sequence of dashes on a display screen.

12. The apparatus of claim 1, wherein the sensors are configured to detect physiological parameters of the period without direct contact with the person.

13. Apparatus for monitoring physiology of a person, comprising:
one or more physiological sensors configured to detect physiological parameters of a person and generate corresponding electrical signals;
a processor configured to analyze the signals from the sensors to determine if the physiological parameters of the person satisfy at least one alert condition; and
an alert system in communication with the processor for providing an alert when at least one of the physiological parameters satisfies an alert condition;
the alert system being further configured to provide an unable-to-measure alert when the processor determines that the signals satisfy an unable-to-measure condition which indicates that at least some of the signals are unreliable.

14. The apparatus of claim 13, wherein the unable-to-measure alert is provided only when the processor determines that the unable-to-measure condition has persisted for a predetermined minimum period of time.

15. The apparatus of claim 13, wherein the unable-to-measure alert comprises an alarm.

16. The apparatus of claim 15, wherein the alarm is provided over a nurse call system.

17. The apparatus of claim 13, wherein the physiological sensors comprise piezoelectric films.

18. The apparatus of claim 13, wherein the unable-to-measure alert is provided on a display in a bedside unit.

19. The apparatus of claim 13, wherein a low level notification is provided when the unable-to-measure condition persists for less than the predetermined minimum period of time.

20. The apparatus of claim 13, further comprising a display in communication with the processor, wherein the unable-to-measure alert comprises a visual indication on the display.

21. The apparatus of claim 19, further comprising a display screen in communication with the processor, and wherein the low level notification comprises a sequence of dashes on the display screen.

22. The apparatus of claim 13, wherein the unable-to-measure alert is a latching alert.

23. The apparatus of claim 19, wherein the low level notification is non-latching.

24. The apparatus of claim 13, wherein the physiological sensors are configured for installation in a motor vehicle to determine the physiology of a person operating the vehicle.

25. The apparatus of claim 24, wherein the physiological sensors are installed in a seat, seatback, headrest or steering wheel in the motor vehicle.

26. The apparatus of claim 25, wherein the processor is installed in the motor vehicle, and the physiological sensors are connected to the processor via hardwiring to transit the signals from the sensors to the processor.

27. The apparatus of claim 25, wherein the processor is installed in the motor vehicle, and the physiological sensors are wirelessly connected to the processor to transmit the signals from the sensors to the processor.

28. The apparatus of claim 24, wherein the alert system alerts the person operating the vehicle to an approaching sleep state or other potentially hazardous physiological condition.

29. The apparatus of claim 24, wherein the physiological sensors are configured to determine movement of the person operating the vehicle.

30. The apparatus of claim 13, wherein the physiological sensors are configured for installation in a chair to determine the physiology of a person sitting in the chair.

31. The apparatus of claim 13, wherein the physiological sensors are configured for installation in a chair to monitor the state of relaxation of a person sitting in the chair.

32. The apparatus of claim 13, wherein the physiological sensors are configured for installation in an aircraft for monitoring the physiology of a person operating the aircraft.

* * * * *